United States Patent [19]
Bates
[11] Patent Number: 4,627,422
[45] Date of Patent: Dec. 9, 1986

[54] VARIABLE TRACTION APPARATUS AND METHOD

[76] Inventor: Thomas J. Bates, 120 Hillcrest Rd., Berkeley, Calif. 94706

[21] Appl. No.: 790,811
[22] Filed: Oct. 24, 1985
[51] Int. Cl.[4] .......... A61F 5/00
[52] U.S. Cl. .......... 128/71; 128/75; 128/68
[58] Field of Search .......... 128/68, 69, 71, 74, 128/75, 78; 272/120, 121, 134, 142, 144

[56] References Cited

U.S. PATENT DOCUMENTS 890,069 6/1908 Koehler .......... 128/71
3,570,479 3/1971 Horn .......... 128/71
4,205,665 6/1980 Burton .......... 128/75 X
4,442,832 4/1984 Ollenberger .......... 128/71

*Primary Examiner*—Stephen F. Husar
*Attorney, Agent, or Firm*—Flehr, Hohbach, Test, Albritton & Herbert

[57] ABSTRACT

Apparatus and method for a traction device utilizes a traction bed freely slidable on a base which is liftable at one end by a remote controlled motorized winch. The person lying on the traction bed controls the winch. The person is tethered to one end of the base by, for example, metal cuffs around the ankles which hook on to a bar on the base. Thus, when the base is lifted, it tilts the traction bed which gradually slides on the base away from the tethered extremity, along with the person who is fastened thereon, to provide a precisely desired amount of tractive force.

8 Claims, 4 Drawing Figures

VARIABLE TRACTION APPARATUS AND METHOD

FIELD OF THE INVENTION

The present invention relates to a traction apparatus for applying continuously-variable, gravitational, tractive force to the body of a human user.

BACKGROUND OF THE INVENTION

Traction is frequently prescribed to treat people suffering from pain in the back, neck or other parts of the body. This pain is often caused by abnormalities of the spinal column, such as misalignment of the vertebrae, slipping or rupture or erosion of the discs betwen the vertebrae, etc., all causing pinching or impingement on the nerves running through the vertebrae and resulting in intense and continuous pain. The proper application of tractive force on the spinal column whereby the vertebrae are eased apart slightly is known to relieve this pressure on the nerves thereby reducing the pain and, in some instances, aiding in curing the underlying cause of the pain.

Various mechanical and electrical devices have been used to apply tractive force to the spinal column of patients in sitting, standing or reclining positions. One way of applying such tractive force to a patient is to tether him at one end or the other of his body, depending on where in his spinal column it is desired to apply the traction, and allowing the weight of his body, through gravity, to provide the tractive force. For example, if it is desired to apply traction to the cervical (neck) vertebrae, the patient is tethered by the chin and suspended therefrom, whereas, if it is desired to apply traction to the lumbar (lower back) vertebrae, he is tethered by the ankles and suspended upside down.

Maximum gravitational tractive force is obtained by suspending the patient in a vertical position. However, not only do most people find the upside-down position (when suspended by the ankles) disorienting and unsettling but, also, the application of 100% of a patient's body weight as a tractive force on his spinal column can be excessive and itself cause pain and even harm. It is necessary, therefore, to find a way of reducing the gravitational tractive force on the patient. This can be done by supporting the patient on an inclinable plane surface while suspending him from one end or the other of his body. The amount of gravitational force can then be adjusted by varying the angle of inclination of the supporting surface. When the inclinable surface is horizontal, the gravitational tractive force is 0% of body weight; i.e., there is no traction. When the inclinable surface is vertical, the gravitational tractive force is 100% of the patient's body weight.

Another force that has to be taken into account when applying gravitational traction in the way outlined above is the friction between the patient and the inclinable surface on which he is lying. At low angles of inclination, this frictional force is greater than the gravitational force so that the patient does not slide down the inclined surface and, therefore, no traction is exerted on his spinal column. It is not until the gravitational force, increased by increasing the angle of inclination of the supporting surface, is greater than the frictional force holding the patient to that surface that the patient can slide down the inclined surface away from the tether to which he is attached and, thus, get the benefit of his body weight as a tractive force on his spinal column.

However, it is essential that, when the gravitational force overcomes the frictional force, it does not do so suddenly or else the patient will be subjected to an abrupt and possibly painful or harmful jerk.

A device that applies gravitational principles is illustrated in U.S. Pat. No. 4,205,665 to Burton. This device comprises an adjustable inclined hospital bed, rotating hoops, and a traction bar. A chest harness is wrapped around the patient's thorax and connected to the traction bar by straps and a tethering cable. The patient is thereby suspended by the rib cage from above his shoulders. The force of gravity on the lower body provides the tractive force on the lower back. This combination of a hospital bed and an elaborate framework is appropriate for use in a hospital, but it is not ideal for use in the home. Moreover, as explained above, the friction caused by contact of the patient with the bed tends to counteract the gravitational pull, particularly at low angles of inclination. As the bed is raised towards the vertical the overcoming of this friction can cause uncomfortable jarring to the patient.

OBJECT AND SUMMARY OF THE INVENTION

It is, therefore, an object of the invention to provide an improved variable traction apparatus and method therefor.

In accordance with the above object, there is provided an apparatus for applying variable traction to a person having a nominal height comprising an elongated base having track means in the elongated direction and having a length in this direction longer than the height of the person. A traction bed including a flat elongated surface allows the person to recline thereon and is mounted for slidable movement in the elongated direction on the track means of said base and substantially parallel to and co-extensive with said base. Means are provided for controllably lifting one end of the base and the associated traction bed and maintaining them at a selected inclination. An extremity of said person reclining on the traction bed is tethered to the lifted end of the base.

Using the foregoing apparatus, a method of applying traction comprises the steps of placing a person on the traction bed in a supine position, tethering an extremity of the person to the end of the base and then lifting that end of the base to which the person is tethered. The lifting means is actuated to lift the end of the base to a desired inclination. It is then stopped, allowing the effect of the weight of the person to slide the traction bed on the base in a direction away from the tethered extremity, thereby placing the person in traction.

Figure 1:
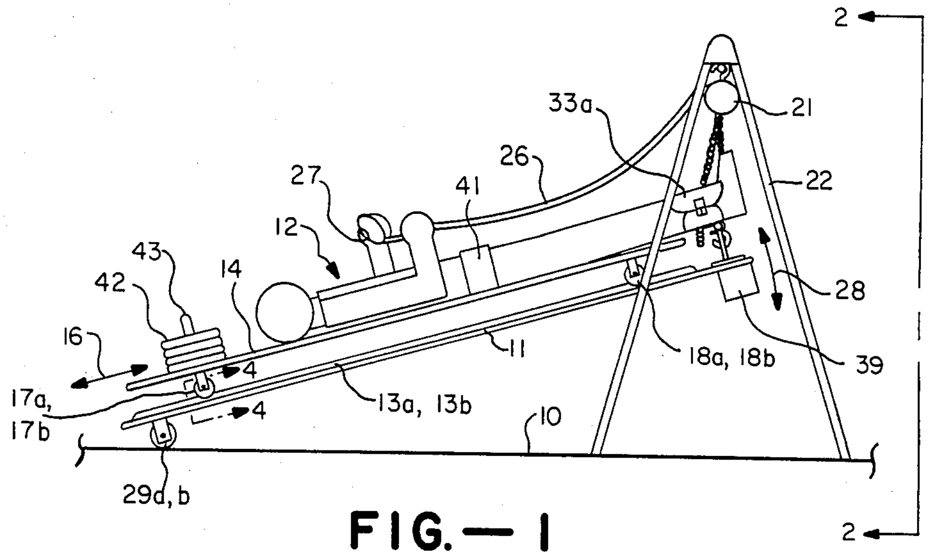
FIG. 1 is a side view of the apparatus embodying the present invention.
Figure 2:
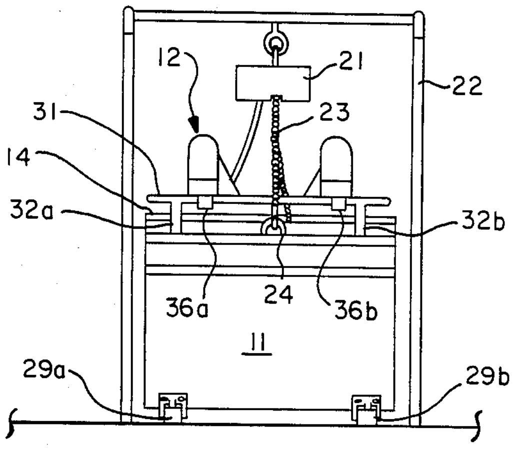
FIG. 2 is an end view of FIG. 1 taken along the line 2—2.

As illustrated in both FIGS. 1 and 2, the traction apparatus of the present invention includes an elongated base 11, which has a length slightly longer in the elongated direction than the height of the person 12 utilizing the apparatus. Base 11 includes a pair of tracks 13*a*, 13*b* formed of angle iron. They are placed in the elongated direction.

The person 12 is placed in a supine position, i.e., reclining on a traction bed 14 which is mounted for slidable movement in the elongated direction illustrated as arrow 16 on the track means 13*a* and 13*b*. Such slidable movement of bed 14 is parallel to the base 11 and substantially co-extensive with it.

Figure 4:
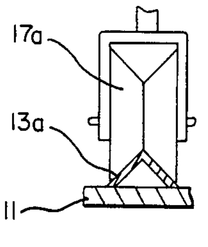
FIG. 4 is a fragmentary view taken along line 4—4 of FIG. 1.

As illustrated in FIG. 1, the bed 14 is slightly shorter than base 11 and as illustrated in FIG. 2, the widths are substantially similar. To provide slidable movement between the traction bed 14 and base 11 mounted on the bottom of bed 14 are a lower pair of rollers 17*a* and 17*b* and an upper pair of rollers 18*a* and 18*b*. Only the first roller of each pair is shown in the drawing. A typical roller 17*a* is better illustrated in FIG. 4 and mates with the track 13*a* to prevent sideways drifting of the traction bed 14 with respect to base 11.

The technique of providing for relative movement between traction bed 14 and base 11 is not a critical one and several alternative constructions are possible. For example, base 11 could include "C" shaped tracks or slits along its sides in which appropriate rollers of bed 14 would track. An additional set of rollers can be used. Alternatively, low friction surfaces, for example, coated with Teflon, might be utilized between base 11 and bed 14.

Base 12 is typically constructed of plywood with suitable reinforcing. However, it could be an open frame or tubular structure on which the tracks 13*a*, 13*b* are mounted.

To allow one end of the combination of base 11 and bed 14 to be lifted, a motorized winch is suspended from the apex of an "A" frame supporting structure 22. The winch is commercially available from several sources. A chain 23 extending therefrom, as shown in FIG. 2, is attached to base 11 by a ring 24. Remote control of winch 21 is provided by a cable 26 which has an operating module 27 controllable by the user 12. Base 11 can be controllably moved from a horizontal position to the position shown in FIG. 1, stopped at any desired inclination and then reversed, as shown by the double-ended arrow 28. Other obvious techniques for providing a selected angle of inclination are a hydraulic ram or a scissors lift. Also rather than the "A" frame support structure 22, the winch 21 could be supported from a ceiling beam.

To allow base 11 to freely move on floor 10 during lifting a pair of rollers 29*a* and 29*b* is mounted at the end of base 11 opposite the lifted end.

An extremity of the person 12, such as the head or the foot, is tethered to the lifted end of base 11.

Figure 3:
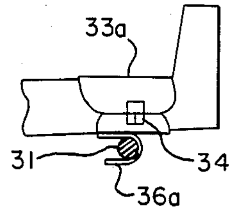
FIG. 3 is a fragmentary view of a tethering portion of FIG. 1.

Such means include a horizontal cross bar 31, as best shown in FIG. 2 mounted to base 11 by legs 32*a* and 32*b*. The user places metal cuffs or ankle-straps 33*a* and 33*b* on his ankles secured by a suitable fastener 34 (see FIG. 3). The cuffs 33*a* and 33*b* are commercially available and known as "inversion boots." Typically a person utilizing these boots hangs himself vertically upside-down from, for example, a bar mounted in the doorway. Each of the boots includes on its rear a hook portion 36*a* and 36*b* which can be hooked around the bar 31, as illustrated in FIG. 3. In place of boots or cuffs 33*a*, 33*b*, suitably configured straps or loops can be used.

A spacing block 39 is attached to the under-side of the lifting end of base 11, the end opposite the floor rollers 29*a* and 29*b*, so that when the base 11 and its associated traction bed 14 are in the lowered position, they will be horizontal to allow for easy access to the apparatus by the person using it.

In order to maintain the user 12 on the traction bed without sliding, especially in steeper inclinations, a standard type of fastening belt 41 (FIG. 1) is provided with a quick release (not shown). This would normally fit around the user's waist.

As illustrated in FIGS. 1 and 2, the person 12 is tethered to the base 11 by the lower extremity; specifically, the feet and ankles as illustrated in FIG. 3. This provides traction in the lower back. Alternatively, but not illustrated, if traction of the cervical vertebrae (neck) is desired, the user lies with the other extremity, the head, at the lifted end of the traction bed 14 and is tethered to the base 11 by a strap that passes around the chin.

Use of the Traction Device

With the base 11 and traction bed 14 in a horizontal position, the user or person 12 lies on bed 14 and, having fastened the cuffs 33*a* and 33*b* to his ankles, places the hooks 36*a* and 36*b* around the bar 31. In this way, an extremity is tethered to that end of base 11 that is to be lifted. Next strap 41 is fastened to ensure there is no sliding in a steeply inclined position. The user then grasps the operating module 27 and actuates lifting device 21 to the desired inclination and stops at that inclination. During this lifting operation, the pair of floor rollers 29*a* and 29*b* facilitate movement of the base 11 along the supporting floor 10. During this lifting operation and thereafter, the weight of the person on the traction bed causes it to slide on the base in a direction away from the tethered extremity, as indicated by the arrow 16; in this case it would be, of course, to the left as shown in the drawing. Thus, the person 12 is now in traction. If greater traction is desired, then weights 42 may be placed on a stud 43 which is fixed to traction bed 14. This allows a greater traction force to be applied at relatively shallower angles of inclination.

The person remains at a fixed angle of inclination for a prescribed period of time and during this period his spinal column is under traction. At the end of the time, the person lowers the traction bed and base to the floor again and treatment ceases. As treatment progresses and tolerance to the traction increases, the person can progressively increase the tractive force by adding weights 42 or by increasing the angle of inclination of the base 11.

Thus, an improved traction device is provided which is simple in construction, can be used in the home, allows for fine, smooth and gradual adjustment of the gravitational tractive force, is operable by the user himself without an assistant and, by providing for almost frictionless movement of the traction bed 14 on the base 11, avoids the risk of sudden tugs on the spinal column of the user 12.

What is claimed:

1. Apparatus for applying variable traction to a person having a predetermined height comprising:

an elongated base having track means in the elongated direction and having a length in said direction longer than said height of said person;

a traction bed including a flat elongated surface for allowing said person to recline thereon, said bed being mounted for slidable movement in said elongated direction on said track means of said base and substantially parallel to and coextensive with said base;

means for controllably lifting an end of said base and said associated traction bed and maintaining at a selected inclination;

means for tethering an extremity of a said person reclining on said traction bed to said lifted end of said base.

2. Apparatus as in claim 1, where said means for controllably lifting an end of said base includes a motorized winch connected to said base and including a remote control device connected to said motorized winch operable by the person reclining on said traction bed to activate said motorized winch in a bi-directional manner.

3. Apparatus as in claim 1, including means for adding a predetermined weight to said traction bed, whereby gravitational tractive force on said person is increased.

4. Apparatus as in claim 1, where said base includes a pair of rollers for rolling on a floor at an end in the elongated direction distant from said tethering means for allowing smooth movement of said base on said floor during said lifting.

5. Apparatus as in claim 1, including means for providing said slidable movement between said traction bed and said base, including at least two pairs of rollers mounted at opposite ends of said traction bed which roll on said track means on said base.

6. Apparatus as in claim 5, where said track means on said base are adapted for mating with said rollers.

7. Apparatus as in claim 1 including means for attaching a said person to said traction bed to prevent slipping between said person and said traction bed when said traction bed is in a lifted position.

8. A method of applying traction to a person using a base with a slidable traction bed mounted thereon and including controllable means for lifting one end of the base comprising the following steps:

placing said person on said traction bed in a supine position and tethering an extremity of said person to the end of said base which is to be lifted;

actuating said lifting means to lift said end of said base to a desired inclination;

stopping said lifting means and allowing the effect of the weight of said person to slide said traction bed on said base in a direction away from said tethered extremity, whereby the spinal cord of said person is in traction.

* * * * *